(12) United States Patent
Shih

(10) Patent No.: US 11,304,358 B2
(45) Date of Patent: Apr. 19, 2022

(54) SYSTEM AND METHOD FOR ANAEROBIC DIGESTION OF ANIMAL WASTES

(71) Applicant: Holistic Farming, Inc. (HFI), Cary, NC (US)

(72) Inventor: Jason Chia Hsing Shih, Cary, NC (US)

(73) Assignee: Holistic Farming, Inc. (HFI), Cary, NC (US)

( * ) Notice: Subject to any disclaimer, the term of this patent is extended or adjusted under 35 U.S.C. 154(b) by 0 days.

(21) Appl. No.: 15/955,927

(22) Filed: Apr. 18, 2018

(65) Prior Publication Data

US 2018/0235139 A1  Aug. 23, 2018

Related U.S. Application Data

(63) Continuation of application No. 14/972,214, filed on Dec. 17, 2015, now abandoned, and a
(Continued)

(51) Int. Cl.
*A01C 3/02* (2006.01)
*C02F 11/04* (2006.01)
(Continued)

(52) U.S. Cl.
CPC ............ *A01C 3/023* (2013.01); *A01C 3/025* (2013.01); *A01K 1/0103* (2013.01); *C02F 11/04* (2013.01); *C05F 17/40* (2020.01); *C05F 17/50* (2020.01); *C12M 21/04* (2013.01); *C12M 45/06* (2013.01); *C12M 45/09* (2013.01); *C12M 45/20* (2013.01); *C02F 2103/20* (2013.01); *Y02A 40/28* (2018.01); *Y02C 20/20* (2013.01); *Y02E 50/30* (2013.01); *Y02P 20/145* (2015.11); *Y02W 10/20* (2015.05); *Y02W 30/40* (2015.05)

(58) Field of Classification Search
CPC ...... A01C 3/023; A01C 3/025; A01K 1/0103; C12M 45/09; C12M 45/20
See application file for complete search history.

(56) References Cited

U.S. PATENT DOCUMENTS

| | | |
|---|---|---|
| 4,040,953 A | 8/1977 | Ort |
| 4,372,856 A | 2/1983 | Morrison |

(Continued)

FOREIGN PATENT DOCUMENTS

| | | |
|---|---|---|
| CA | 576500 A | 5/1959 |
| CA | 2510672 A1 | 12/2005 |

(Continued)

OTHER PUBLICATIONS

Shih, Jason C.H., "Anaerobic Biotechnology", Chapter 14—Development of Anaerobic Digestion of Animal Waste: From Laboratory, Research and Commercial Farms to a Value-Added New Product, pp. 339-352, Imperial College Press, 2015.
(Continued)

*Primary Examiner* — Lydia Edwards
(74) *Attorney, Agent, or Firm* — James G. Passé; Passé Intellectual Property, LLC

(57) ABSTRACT

A new method of disposing of waste for the hog industry is disclosed which avoids use of lagoons. Manure is semi-continuously degritted, anaerobically digested and digested with biomass to produce bio-organic fertilizer and biogas.

7 Claims, 3 Drawing Sheets

Related U.S. Application Data continuation-in-part of application No. 13/793,140, filed on Mar. 11, 2013, now abandoned.

(51) Int. Cl.

| | | |
|---|---|---|
| *C05F 17/40* | (2020.01) | |
| *C12M 1/107* | (2006.01) | |
| *C12M 1/00* | (2006.01) | |
| *C05F 17/50* | (2020.01) | |
| *A01K 1/01* | (2006.01) | |
| *C02F 103/20* | (2006.01) | |

(56) References Cited

U.S. PATENT DOCUMENTS

| | | | | |
|---|---|---|---|---|
| 5,525,229 | A | 6/1996 | Shih | |
| 6,207,057 | B1* | 3/2001 | White | A01K 1/0103 |
| | | | | 210/609 |
| 6,764,600 | B2 | 7/2004 | Cha et al. | |
| 6,860,997 | B1* | 3/2005 | Frederick | C02F 3/286 |
| | | | | 210/259 |
| 7,081,199 | B2 | 7/2006 | Leskow | |
| 7,179,642 | B2 | 2/2007 | Dvorak | |
| 7,306,731 | B1 | 12/2007 | Dewaard | |
| 7,371,328 | B1 | 5/2008 | Hokanson et al. | |
| 2003/0201225 | A1* | 10/2003 | Josse | C02F 1/56 |
| | | | | 210/605 |
| 2005/0035059 | A1* | 2/2005 | Zhang | B01D 61/04 |
| | | | | 210/605 |
| 2006/0283805 | A1* | 12/2006 | Schreppel, Jr. | C02F 1/38 |
| | | | | 210/721 |
| 2008/0098780 | A1* | 5/2008 | Shubin | B01F 7/241 |
| | | | | 71/9 |
| 2009/0282882 | A1* | 11/2009 | Verhave | C05F 17/0018 |
| | | | | 71/7 |
| 2012/0055861 | A1 | 3/2012 | Conwell | |
| 2014/0251899 | A1 | 9/2014 | Shih | |
| 2014/0251903 | A1* | 9/2014 | Shih | C02F 3/286 |
| | | | | 210/612 |

FOREIGN PATENT DOCUMENTS

| | | |
|---|---|---|
| GB | 1437336 | 5/1976 |
| WO | 2010048225 A2 | 4/2010 |

OTHER PUBLICATIONS

Database WPI Week 201307 Thomson Scientific, London, GB; AN 2013-A86626 & WO 2013/006086 A1 (Mandelshtam A S) Jan. 10, 2013 (Jan. 10, 2013).

\* cited by examiner

US 11,304,358 B2

SYSTEM AND METHOD FOR ANAEROBIC DIGESTION OF ANIMAL WASTES

This application is a continuation application of U.S. non-provisional application Ser. No. 14/972,214 filed on Dec. 17, 2015, and a continuation in part of US non-provisional application Ser. No. 13/793,140 filed Mar. 11, 2013 and which are incorporated herein in their entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

Field of the Invention

The present invention relates to the anaerobic treatment of animal waste, especially waste from hog houses, without use of a lagoon or composting.

Description of Related Art

One of the natural products of raising animals for food production is the accumulation of animal waste, i.e. manure. Very large production facilities can produce incredible amounts of waste. Specifically, hog farms are known for the large amount of waste produced and the trouble with getting rid of the waste produced by them.

A typical hog house is about one hundred sixty feet long and forty feet wide, housing roughly 1,100 hogs, which take roughly 6 months to mature for market slaughter. Waste is currently removed by use of water flushing from the hog house. While several means of fecal treatment have been proposed for the hog house, the most common means of disposal at the moment is to flush the water and waste into a lagoon for treatment. Alternatively, high concentration manure is processed by composting aerobically.

Lagoons are subject to several problems. Fluid from the lagoons is normally sprayed over crops. The solid material is allowed to decay in the lagoon and/or spread out over crop fields. This causes complaints about unacceptable odors from the fields and surrounding areas. Another problem is that storms or other flooding conditions can occur, causing waste and their associated pathogens to reach the surface and underground water. This causes problems for local municipalities or others that rely on that water table for drinking water.

North Carolina is the second largest pork producing state and has been plagued by the quantity of hog lagoons and their associated problems. The large hog farms can produce tons of waste daily, leaving entire counties saddled with the odor and problems of this waste treatment method. Because of such problems, the North Carolina legislature has curtailed the construction of new hog farms, awaiting solutions for the treatment of hog farm waste. There is still, therefore, a need to find an acceptable alternative to the lagoon process, which until now has not had a practical solution. Naturally, the problem is not in North Carolina alone. Around the world, large scale pig farms and animal farms of other species, such as poultry and dairy, are facing the similar problems as well.

BRIEF SUMMARY OF THE INVENTION

The present invention relates to an alternative solution for the remediation of a hog house manure wherein the waste is degritted, digested and co-digested with biomass, to produce biogas energy and organic fertilizer without the horrid odor and other problems of the prior art. In one embodiment, the degritter, the anaerobic digester, and the secondary digester are modular in design for fitting together easily into a unitary structure for daily or semi-continuous processing. In order to make the system compact and efficient, it has to be insulated and operated at thermophilic temperatures, i.e. 50°-60° C.

Accordingly, in one embodiment, the present invention relates to a method for the semi-continuous treatment of animal waste from an animal containment building comprising:
  a) periodically removing undiluted animal waste from the animal containment building;
  b) placing the removed waste in a hydrolytic degritting chamber with sufficient heated water or steam to obtain a mixture of at least about 50 degrees C. to about 60 degrees C. and degritted;
  c) transfer of the degritted mixture into an anaerobic digester chamber held at a temperature of about 50 degrees to about 60 degrees C. and digested; and
  d) transfer of at least a portion of the digested mixture to a secondary solid phase digester chamber, loaded with dry biomass and fermenting the mixture at a temperature of at least about 50 degree C. and removing the bio-organic fertilizer from the solid-phase digester.

In another embodiment, the invention relates to a system for the semi-continuous treatment of animal waste from an animal containment building;
  a) one or more animal containment buildings containing animal waste;
  b) a hydrolytic degritter in fluid communication with an anaerobic digester chamber, which is in turn in fluid communication with a secondary solid phase digester chamber, all in an insulated unitary structure wherein communication is accomplished by flow pressure;
  c) heated water or steam to combine with animal wastes from the one or more containment buildings sufficient to raise the combined temperature to about 50 degrees C. to about 60 degrees C.; and
  d) wherein the animal waste from the animal containment building is then in fluid communication with the hydrolytic degritter.

DETAILED DESCRIPTION OF THE INVENTION

Figure 1:
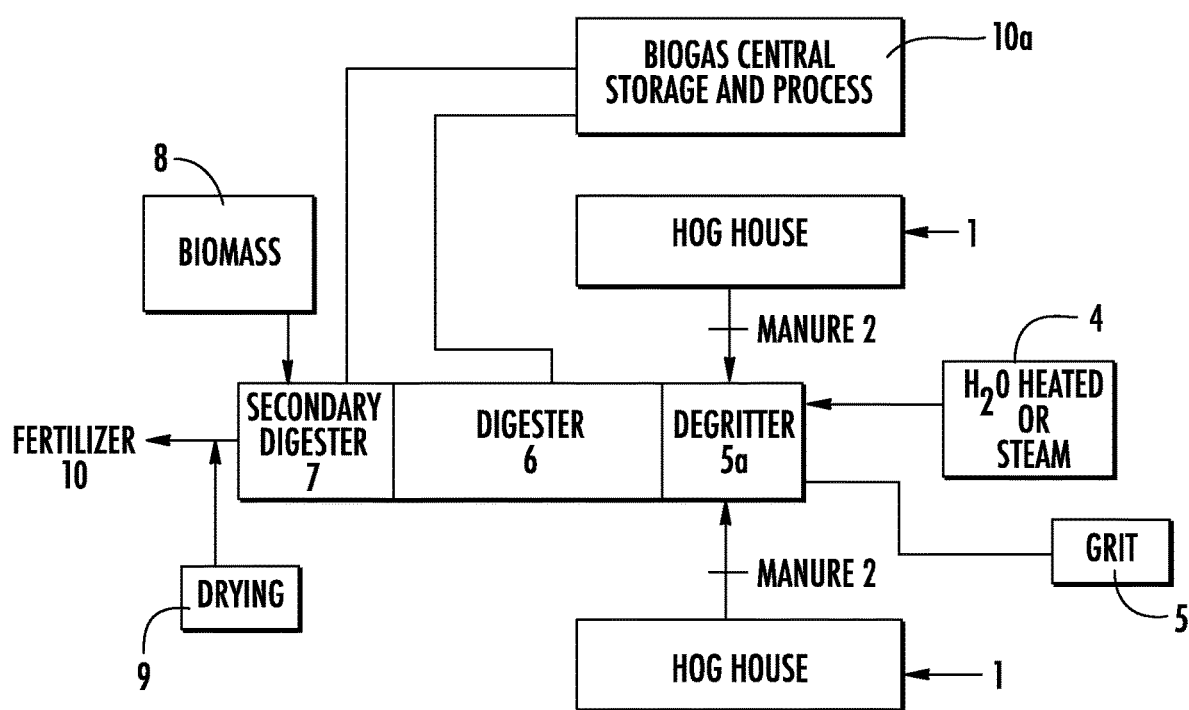
FIG. 1 is a depiction of the system of the present invention.

While this invention is susceptible to embodiment in many different forms, there is shown in the drawings, and will herein be described in detail, specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings. This detailed description defines the meaning of the terms used herein and specifically describes embodiments in order for those skilled in the art to practice the invention.

Definitions

The terms "about" and "essentially" mean±10 percent.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

The term "comprising" is not intended to limit inventions to only claiming the present invention with such comprising language. Any invention using the term comprising could be separated into one or more claims using "consisting" or "consisting of" claim language and is so intended.

References throughout this document to "one embodiment", "certain embodiments", and "an embodiment" or similar terms means that a particular feature, structure, or characteristic described in connection with the embodiment is included in at least one embodiment of the present invention. Thus, the appearances of such phrases in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are for the purpose of illustrating certain convenient embodiments of the present invention, and are not to be considered as limitation thereto. The term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein, the term "grit" refers to insoluble sandy matter that exists within the animal waste such as hog, poultry and dairy manure waste. The term "animal waste" refers to any of the waste type of animal manure, such as hog, poultry and dairy manure, which would be used in an anaerobic digestion system and containing grit. Animal waste is transferred periodically, e.g. in one embodiment, daily, from the animal containment building to the degritter chamber. Though one skilled in the art could choose appropriate times e.g. every 12, 24, 36, and 48 hours, etc.

As used herein, the term "degritter chamber" refers to a space designed for holding and hydrolyzing organic waste with hot water or steam at an elevated temperature. A chamber can be made of any material, such as a stainless steel, fiberglass or concrete chamber, and the tank, in one embodiment, has to be insulated to better hold the elevated temperature without the need for additional heating apparatus throughout the entire process once heated water is added. The elevated temperatures (from about 50 degrees C. to about 60 degrees C.) facilitate hydrolysis and the separation of grit and enough heated water is added or steam is injected to raise the mixture to this temperature. The hydrolyzed and degritted slurry is transferred and, in one embodiment, forced, by the periodic incoming manure and hot water (see Figures), under flow pressure into the anaerobic digester chamber (see e.g. FIG. 3). After the operation for a selected period of time, the grit accumulates at the bottom of the hydrolysis chamber by sedimentation. It can be removed by a pump or with a gravity bottom drain, such as a conical area, to remove the grit by bleeding off the grit. This can be done periodically, e.g. daily or the like.

The operation in each chamber or system is semi-continuous, feeding with manure and discharging organic fertilizer periodically (e.g. daily or the like). As a plug-flow system, i.e. fluid gravity transfer, in one embodiment, the liquefied material flows from a degritter chamber where it stays one day, to a horizontal anaerobic digester tank (in one embodiment fluid gravity) where it is retained for at least about 10 days (in one embodiment, about 10-15 days), then the digester mixture (the digestate) to the secondary solid-phase digester for 1-5 days and finally discharged as organic fertilizer. The operation of the complete system is a semi-continuous process to keep hog houses clean. Plug-flow then relies on newly added wastes and water added to the degritter pushing the degritted material through the system. So, in one embodiment where waste is added daily to the degritter, the chamber is just large enough for one day's worth of mixture (water and manure). Adding the next day's mixture pushes the first mixture to the second chamber and, depending on the length (size) of the second chamber will determine the length of the mixture's stay in that chamber and so on. In one embodiment, the anaerobic chamber is 10 times the size of the degritter chamber i.e. remains for ten days (the retention time) when one day in the degritter.

The method of the present invention involves adding the organic waste, such as hog manure, to the degritter chamber. This can be done by scraping or the like without diluting the manure till it reaches the degritter chamber. Hot water is added to, or steam is injected into, the chamber to obtain a slurry mixture, wherein the final mixture is at about 50 degrees C. to about 60 degrees C., and the mixture is held at that temperature in the tank by insulation, rather than heating the tank contents further. In general, one skilled in the art can obtain the optimum percentage of solids, and thus, the proper amount of water, and its temperature, based on the weight of the manure added by simple testing of the process. In one embodiment, a 1:1 ratio of hot water is added to manure in the degritter chamber to give the percent total solids 5% to 10% on a weight/weight basis. Alternatively, steam can be injected into the degritter to raise the temperature and to reach 5% to 10% total solids concentration. In one embodiment, the hydrolytic degritter process takes one day. Next day, fresh manure from the hog house is scraped into the degritter and hot water added to force out at least a portion of the degritted mixture to flow into the large digester tank. Grit can be removed as described above.

Once the mixture is degritted, it is transferred, and, in one embodiment, it flows under a hanging wall, to a connected horizontal chamber of an anaerobic digester for anaerobic digestion and for production of biogas. As used herein, "anaerobic digestion" is a process in which microorganisms break down biodegradable material in the absence of oxygen to produce a lower solids liquid effluent. The digestion process begins with bacterial hydrolysis of the input materials to break down insoluble organic polymers, such as carbohydrates, proteins and lipids and make them available for other bacteria. Acidogenic bacteria then convert the sugars and amino acids into carbon dioxide, hydrogen, ammonia, and organic acids. Finally, methanogens convert these products into a gas mixture of methane and carbon dioxide called biogas which can be collected and utilized. The methanogenic archaea populations play an indispensable role in anaerobic treatments. Biogas can be collected into a flexible and inflatable plastic membrane cover on top of the digester tank, where the biogas, in turn, can be pumped to a large central gas storage station for further process and utilization. At this digestion stage, it takes a time of at least 10 days (ten times the digester volume/daily feeding volume) for the mixture called "digestate" to flow to the next stage. The digestion in this stage is kept in the insulated chamber at about 50 to about 60 degrees C. The whole system can be housed with a roof to lower the heat loss.

It is used as part of the process to treat biodegradable waste. As part of an integrated waste management system that produces, captures and utilizes biogas, it reduces the emission of greenhouse gases into the atmosphere. Anaerobic digesters can also be fed with purpose-grown energy crops, such as maize, crop waste and grasses for co-digestion.

The process of the invention produces a biogas, consisting of methane, carbon dioxide and traces of other "contaminant" gases. This biogas can be used directly as gaseous fuel for heat and de-sulfured for power generation, or upgraded to natural gas-quality biomethane for transportation fuel. The use of biogas as a fuel helps to replace fossil fuels. Also, the nutrient-rich digestate produced can be concentrated into liquid fertilizer, or further processed into bio-organic fertilizer. The liquid effluent or digestate from this stage is passed to the third stage tank. In one embodiment, the biomass is pre-loaded in another embodiment, the discharged digestate is sprayed over the biomass (see FIG. 3).

The discharged digestate from the anaerobic digester chamber is transferred to a secondary solid phase digester pre-loaded with dry biomass for further fermentation of the mixture at about 50-60 degrees C. In one embodiment, the secondary digester is insulated and does not contain heaters.

As used herein, the term "biomass", refers to plant materials, including miscanthus, switchgrass, prarie grasses, hemp, corn, poplar, willow, sorghum, sugar cane, a variety of tree species, and crop or vegetable wastes. Typically, these plant materials are rich in polysaccharides, and are collectible and dryable.

In one embodiment, the biomass solids are loaded in the chamber of the secondary digester prior to adding digestate. The digestate is added (e.g. by spraying) daily on top of the biomass (in one embodiment at a ratio of 1:1 by weight) and kept in the insulated chamber for fermentation. The temperature of the effluent is kept at about 50 to about 60° C.—the mixture is not further heated and the chamber is insulated to hold the temperature without further heating. The mixture is fermented for a period of about one day or longer.

The resulting product is high in solids, at about 30% to about 50%. The liquid is separated by leaching, pressing or drying. The high solids material, which is >50%, can then be utilized as a bio-organic fertilizer or as desired. More biogas can be collected into an inflatable membrane cover on top from this step as well.

As used herein, the term "semi-continuous" refers to the present periodic process which removes materials from the animal containment building at regular periodic intervals, such as daily, every other day, etc., and adds the materials, with hot water or steam, into the degritter chamber during the animal growing season. The process of semi-continuous manure feeding will push the internal mixture by gravity flow and mixing in the digester. The digestate will be discharged daily into the secondary solid-phase digester to produce bio-organic fertilizer and more biogas depending on the amounts and frequency added.

As used herein, the term "animal containment building" refers to the building that farm animals are grown in, such as the building hogs are grown in, usually for 6 months or so at a time, i.e. a hog house.

As used herein, the term "animal growing season" refers to the time animals remain in the animal containment building before removal for slaughter, e.g. growth time for a hog.

Figure 3:
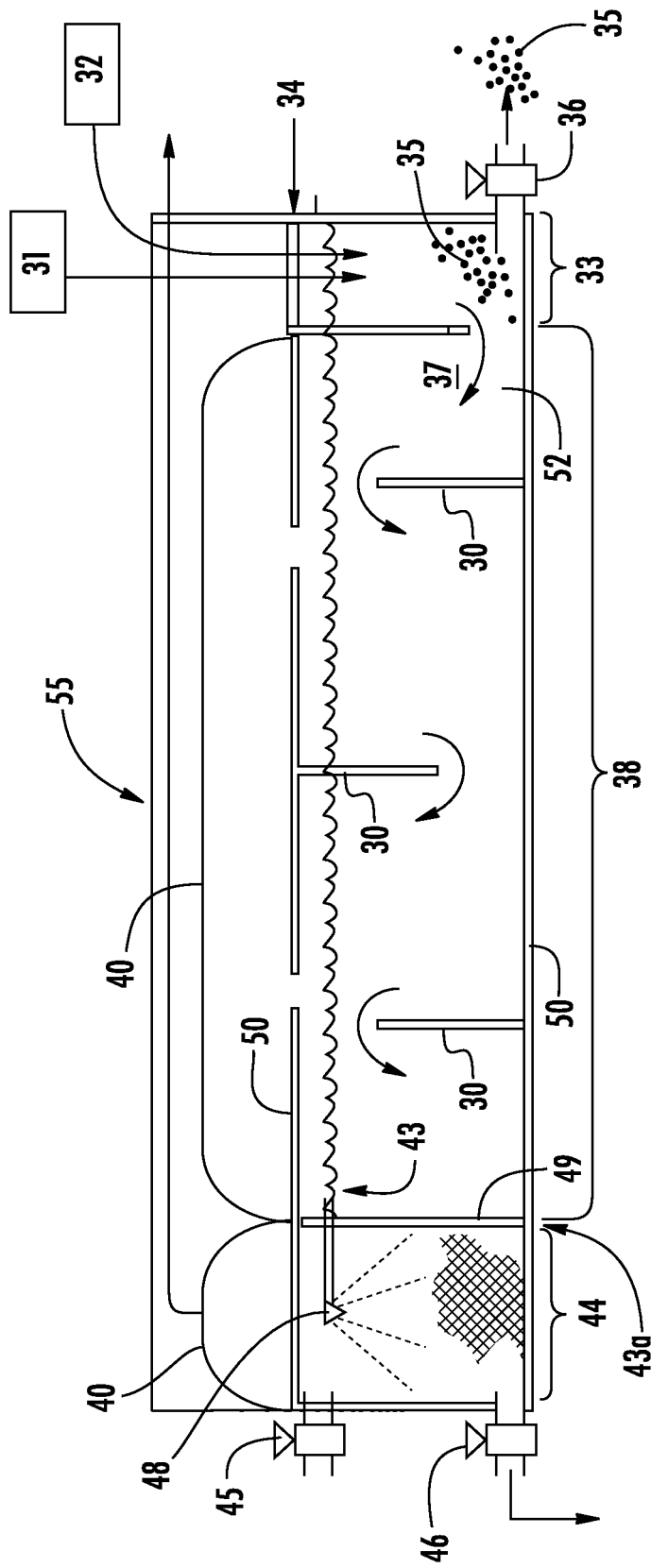
FIG. 3 is a cutaway side view of the modular system unitary structure of the present invention.

As used herein, the term "modular" refers to the components in a unitary building flow system i.e. a degritter, an anaerobic digester, and a secondary digester, that can be swapped out and are interchangeably modular and designed to fit together as a single unit or unitary structure, rather than separate components just connected by piping or the like. An example is shown in FIG. 3. The modules can be custom made or pre-made as desired.

DRAWINGS

FIG. 1 is the system of the present invention which depicts a flow system in a unitary building. In this method, there are two hog houses 1 which have hogs for a period of about six months wherein the manure 2 is collected daily, e.g. by scraping, without water dilution and transferred to a hydrolytic degritter 5a along with heated water or steam generating system 4 that is to raise the mixture to about 50 degrees C. to about 60 degrees C. Grit is disposed 5 and the degritted mixture flows under a wall from the addition of more mixture to the degritter, to an anaerobic digester 6 for at least around ten days (retention time: ten days in one embodiment) and then flow to secondary digester 7 loaded with a quantity of biomass 8. The mixture in the secondary digester 7 is left for at least twenty four hours before removing and, optionally, drying 9 to produce dry organic fertilizer 10 which can be easily bagged and sold. Biogas is first collected from the flexible top of primary and secondary digesters and then pumped to central storage 10a. The whole system can be covered by a roof 55.

Figure 2:
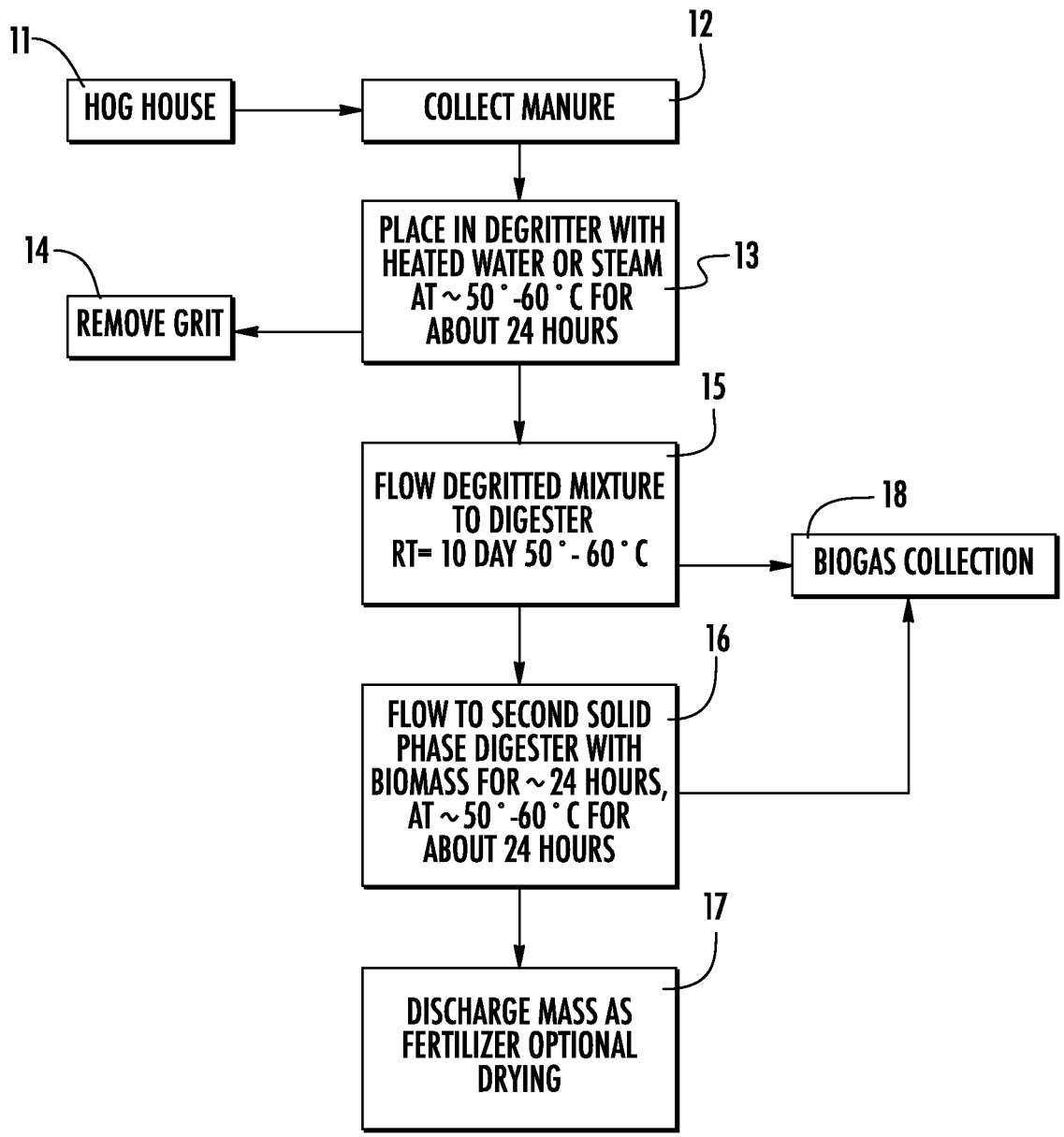
FIG. 2 is a flow chart of an embodiment of the method of the present invention.

FIG. 2 depicts the method of the present invention with a hog house embodiment. Hog house 11 is full of hogs for about six months during annual growing season. Manure is scraped and collected 12 from the hog house 11 and placed in the hydrolytic degritter chamber with heated water or steam sufficient to raise the mixture to about 50 degrees C. to about 60 degrees C. for about twenty four hours (in one embodiment) 13. Grit is removed 14 periodically, as needed. Degritted slurry mixture flows to the anaerobic digester and, upon addition of more manure and water to the degritter, continues to flow into the secondary digester where it ferments for about ten days where Retention Time=ten days 15.

The digestate overflows (flows over a wall) into the secondary digester loaded with biomass and incubated for one day or longer 16, followed by discharge as organic fertilizer with optional drying 17. As indicated, biogas collected from the top of the two digesters can be pumped to a central storage 18. Flow pressure causes all of the mixture to be pushed through the system.

FIG. 3 depicts a side cutaway view of a modular system of the present invention wherein modular components fit together to form a unitary structure with flow through architecture. In this view, manure scrapings 31 from a containment building and hot water or steam 32 are combined and placed into the connected degritter chamber 33 by removing slab 34 and placing manure 31 and hot water 32 inside. Grit 35 is removed via grit valve 36 at the bottom of degritter chamber 33.

Degritter slurry 37 from degritter chamber 33 enters the anaerobic digester chamber 38 by pressure from further added manure and water, which allows a primary digestion of slurry 37 passing over and under walls 30, while biogas emitted is collected by biogas membrane 40 and transported to a central gas storage. The anaerobic digester chamber is about ten times the volume of the degritter, allowing a ten day retention time in the system as the mixture flow through the system.

Digested liquid 43, after about a ten day retention time, overflows wall 43a to the modular secondary solid phase digester 44 (which is loaded with biomass 45) via spray nozzle 48 and fermented for at least twenty-four hours or longer before removal via outlet 46 of fertilizer which can optionally be dried further. It is noted that the structure is insulated 50 so that no heaters are required other than to heat the water added to the manure. More biogas will be collected 40 and pumped to the central gas storage.

Example

In one example, the manure scrapings from two hog houses of approximately 11 tons per day is added, with 11 tons of hot water or steam injected to furnish a temperature of about 50 degrees C. to about 60 degrees C. added to an insulated hydrolytic degritter of the type from FIG. 3 for 24 hours without further heating. The slurry flows daily, minus grit, to an anaerobic digester for a period of 10 days without further heating. A portion (e.g. 10%) of the amount in the digester overflows semi-continuously to a secondary digester loaded with 22 tons of dry biomass and incubated for twenty four hours or longer and the discharge is semi-dried. So each cycle is about twenty four hours and fed with manure on a daily basis to produce both fertilizer and biogas.

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials and the like apparent to those skilled in the art still fall within the scope of the invention as claimed by the applicant.

What is claimed is:

1. A method for the semi-continuous treatment of animal manure without the use of a lagoon, an internal heater, or composting and placed in a hydrolytic degritting chamber of a single unitary structure, the method consisting of:

a) providing a single unitary structure not having an internal heater and having a roof, sides and a bottom that is completely enclosed, wherein the single unitary structure is insulated sufficiently to hold a temperature of about 50 to about 60 degrees C., wherein there is a hydrolytic degritter chamber, an anaerobic digester chamber, and a secondary digester chamber arranged linearly in the single unitary structure;

b) wherein the hydrolytic degritter chamber is positioned in a first end of the single unitary structure for receiving directly into the hydrolytic degritter chamber, the animal manure and steam, or hot water which is designed to create a degritted manure slurry;

c) wherein the anaerobic digester chamber is designed to create a digestate, the anaerobic digester chamber positioned continuous with and next to the hydrolytic degritter chamber, wherein mixing is accomplished by a series of at least 3 partial walls inside the single unitary structure, and a linear current is created in the single unitary structure by the addition of steam or hot water and animal manure to the anaerobic digester chamber which digestate moves over or through a wall into a secondary solid-phase digester chamber in a second end of the single unitary structure positioned next to the anaerobic digester chamber, the secondary solid-phase digester chamber preloaded with dry biomass, which is designed to further digest the digestate and create a high solids product;

d) adding heated water or steam to the hydrolytic degritting chamber in a first end of the single unitary structure to combine with animal manure in the first end of the single unitary structure to form a degritted manure slurry wherein the heat of the heated water or steam is sufficient to raise the temperature in the single unitary structure from about 50 degrees C. to about 60 degrees C., wherein the single unitary structure is insulated sufficiently to hold a temperature from about 50 degrees C. to about 60 degrees C. during the entire method, without the use of an internal heater;

e) moving the degritted manure slurry by horizontal flow pressure, under a first hanging partial wall into a first end of an anaerobic digester chamber of the single unitary structure wherein the manure slurry flows in the anaerobic digester chamber over and under at least 3 additional partial walls between the first end and a second end of the anaerobic digester chamber of the single unitary structure, wherein the at least 3 additional partial walls alternate between a wall hanging from the top of the anaerobic digester chamber and a wall projecting upwards from the bottom of the anaerobic digester chamber allowing the manure slurry to mix and digest; and f) transfer by horizontal flow pressure of the mixed and digested manure slurry at the second end of the anaerobic digester chamber to a secondary solid-phase digester chamber, loaded with dry biomass and fermenting the mixture at a temperature from about 50 degrees C. to about 60 degrees C. and removing a resulting bio-organic fertilizer from the secondary solid-phase digester space.

2. The method for the semi-continuous treatment of animal manure in a single unitary structure according to claim 1 wherein the animal manure is from hogs.

3. The method for the semi-continuous treatment of animal manure in a single unitary structure according to claim 2 wherein the animal manure and heated water or steam are left in the hydrolytic degritting chamber for about 24 hours before removal.

4. The method for the semi-continuous treatment of animal manure in a single unitary structure according to claim 3 wherein the degritted manure slurry flows into the anaerobic digester chamber with at least a 10-day hydraulic retention time.

5. The method for the semi-continuous treatment of animal manure in a single unitary structure according to claim 1 wherein the bio-organic fertilizer removed from the secondary solid-phase digester chamber is further dried before use.

6. The method for the semi-continuous treatment of animal manure in a single unitary structure according to claim 1 wherein biogas is collected for use in both steps e) and f).

7. The method for the semi-continuous treatment of animal manure in a single unitary structure according to claim 1 wherein degritting is accomplished by hydrolysis and sedimentation.

* * * * *